US00PP08991P

United States Patent [19]

Sanford et al.

[11] Patent Number: Plant 8,991

[45] Date of Patent: Nov. 29, 1994

[54] STRAWBERRY SENECA

[75] Inventors: John Sanford, Geneva, N.Y.; Donald Ourecky, Fort Lauderdale, Fla.; Jack Reich, II, Geneva; Kevin Maloney, Clifton Springs, both of N.Y.

[73] Assignee: Cornell Research Foundation, Inc., Ithaca, N.Y.

[21] Appl. No.: 22,948

[22] Filed: Feb. 26, 1993

Related U.S. Application Data

[63] Continuation of Ser. No. 757,051, Sep. 9, 1991, abandoned.

[51] Int. Cl.[5] ..... A01H 5/00

[52] U.S. Cl. ..... Plt./48

[58] Field of Search ..... Plt. 48, 49

[56] References Cited

U.S. PATENT DOCUMENTS

Plt. 7865 5/1992 Izsak et al.....Plt./48

OTHER PUBLICATIONS

Sanford et al, Advances in Strawberry Production 4:39–44 (1985).

"New York's Food and Life Science Bulletin" No. 136, 1991 (Sep. 1991).

Great Lakes Fruit Growers News, Oct. 1991 p. 22.

"American Fruit Grower" Dec. 1991; cover photo and p. 9.

Great Lakes Fruit Growers News, Nov. 1991, p. 60.

*Primary Examiner*—James R. Feyrer

*Assistant Examiner*—Erich E. Veitenheimer

*Attorney, Agent, or Firm*—Jones, Tullar & Cooper

[57] ABSTRACT

A new and distinct variety of strawberry (Fragaria×Ananassa) which is exceptional in combining large yield, potential large fruit size, extreme fruit firmness and good fruit quality. The strawberry is named 'Seneca' and was tested as NY 1529.

9 Drawing Sheets

This application is a continuation of application Ser. No. 07/757,051, filed Sep. 9, 1991 now abandoned.

BACKGROUND OF THE INVENTION

This new cultivar was developed by the small fruits breeding program of the Department of Horticulture Sciences, Cornell University, Geneva, N.Y., 14456. It was selected in 1976 from 243 progeny of a cross between NY 1261×'Holiday'. (NY 1261 being a cross of 'Redcoat' and NY 844; with 'Redcoat' in turn being a cross of 'Redglow' and NY 254; NY 254 in turn being a cross of Tenn, Shipper and Fairfax. The NY 1261 ×Holiday cross was made in 1974. As a selection the new cultivar was tested as NY 1529. It was tested for many years in second test plots, and was evaluated in replicated yield trials in 1981 and 1982. It was further evaluated at numerous sites throughout the Great Lakes States by cooperative testers. In the fall of 1991, NY 1529 will be publicly released as 'Seneca'.

DESCRIPTION OF RELATED ART

NY 1529 has moderate vigor and runnering growth habit, its leaves are medium green in color, corresponding to Green 137B of the R.H.S. Colour Chart, and foliage is opened and not cupped. NY 1529 leaf serrations are less deeply serrated in comparison with 'Earliglow'. Glandular hairs on the flower pedicel epidermis of NY 1529 run almost parallel with the pedicel, similar to 'Earliglow'. In contrast, glandular hairs on 'Honeoye' are perpendicular to the pedicel and may point slightly downward. The glandular hairs on NY 1529 are much less dense then 'Allstar'.

Table 1 sets forth mean maturity dates based on a 1982 field trial. Mean date of harvest was calculated on a weighted basis. Means followed by the same letter are not significantly different, based on Waller and Duncan's BSD test, K=100.

Table 2 sets forth mean subjective fruit skin toughness scores. Skin toughness was subjectively determined by rubbing the skin of several berries in the hand from each replicate of each genotype. Each plot at each harvest (replicate) was scored independently. Each genotype was rated 1 to 9 with '9' being most resistant to skin abrasion.

Table 3 sets forth mean Instron measurements from 1982 (firmest fruit listed first). Each genotype mean score reflects the force required for the Instron probe to penetrate the flesh of undamaged berries. Twelve berries were tested of each genotype on the same day of harvest for each harvest date. Means followed by the same letter are not significantly different, based on Waller and Duncan's BSD test, K=100.

Table 4 sets forth mean berry weight of 29 strawberry genotypes based upon 1982 field trials. Mean berry weight was determined by dividing total yield per plot by total number of berries per plot. Means followed by the same letter are not significantly different based on Waller and Duncan's BSD test, K=100.

Table 5 sets forth mean subjective fruit appearance scores. Berries were rated 1 to 9 with '9' being the most attractive. Each plot at each harvest (replicate) was scored independently. Means followed by the same letter are not significantly different, based on Waller and Duncan's BSD test, K=100.

Table 6 sets forth mean subjective flavor scores. Berries were rated 1 to 9 with '9' being best flavor. Each plot at each harvest (replicate) was scored independently. Means followed by the same letter was not significantly different, based on Waller and Duncan's BSD test, K=100.

Table 7 shows fruit yields in 1981 and 1982. Means followed by the same letter are not significantly different, based on Waller and Duncan's BSD test, K=100.

Table 8 sets forth the findings of two years of taste panel evaluations.

Table 9 sets forth the mean ranking of 29 cultivars and selections, averaged over 8 characteristics.

Table 10 sets forth the relative performance of NY 1529 at numerous test sites throughout the Great Lakes Region.

TABLE 1

Mean maturity date of NY 1529 vs. other cultivars

| Genotype | Mean Weighted Date of Harvest | |
|---|---|---|
| 'Earlidawn' | June 23 | A |
| 'Midland' | June 24 | AB |
| NY 1402 | June 25 | ABC |
| MDUS 4380 | June 26 | BCD |
| 'Lester' | June 26 | BCD |
| MDUS 4355 | June 26 | BCD |
| NY 1524 | June 26 | BCD |
| MDUS 4774 | June 26 | BCD |
| 'Catskill' | June 27 | CDE |
| NY 1560 | June 27 | CDE |
| 'Honeoye' | June 28 | DEFG |
| 'Holiday' | June 28 | DEFG |
| NY 1530 | June 28 | DEFG |
| MDUS 4579 | June 28 | DEFGH |
| 'Raritan' | June 28 | DEFGHI |
| NY 1570 | June 29 | EFGHIJ |
| NY 1333 | June 29 | FGHIJK |
| MDUS 4426 | June 29 | FGHIJK |
| 'Jewel' | June 30 | GHIJKL |
| NY 1529 | July 1 | HIJKLM |
| NY 1368 | July 1 | HIJKLMN |
| NY 1431 | July 1 | IJKLMN |
| NY 1406 | July 1 | IJKLMN |
| NY 1580 | July 1 | JKLMN |
| 'Allstar' | July 1 | JKLMN |
| 'Canoga' | July 2 | KLMN |
| 'Scott' | July 2 | LMN |
| 'Sparkle' | July 3 | MN |
| NY 1482 | July 4 | N |

TABLE 2

Mean subjective fruit skin toughness scores for NY 1529 and other cultivars.

| Treatment | Replicates | Mean Score | |
|---|---|---|---|
| NY 1524 | 6 | 7.7 | A |
| NY 1529 | 5 | 7.6 | AB |
| 'Jewel' | 5 | 7.4 | AB |
| NY 1530 | 6 | 7.2 | ABC |
| MDUS 4426 | 5 | 7.0 | ASCD |
| NY 1368 | 5 | 6.8 | ABCDE |
| MDUS 4579 | 5 | 6.8 | ABCDE |
| 'Holiday' | 8 | 6.8 | ABCDE |
| NY 1580 | 3 | 6.7 | ABCDEF |
| 'Canoga' | 4 | 6.5 | ABCDEF |
| 'Scott' | 8 | 6.5 | BCDEF |
| 'Lester' | 7 | 6.3 | BCDEF |
| 'Allstar' | 4 | 6.2 | BCDEFG |
| NY 1333 | 5 | 6.0 | CDEFG |
| NY 1406 | 9 | 5.9 | DEFG |
| MDUS 4335 | 6 | 5.8 | DEFG |
| MDUS 4774 | 5 | 5.6 | EFGH |
| NY 1482 | 4 | 5.5 | EFGHI |
| NY 1560 | 4 | 5.3 | EFGHI |
| NY 1402 | 5 | 5.2 | FGHI |
| NY 1431 | 5 | 5.2 | FGHI |
| 'Raritan' | 7 | 5.0 | GHI |
| 'Honeoye' | 7 | 4.5 | HIJ |
| MDUS 4380 | 6 | 4.3 | IJK |
| 'Sparkle' | 5 | 3.8 | JK |
| 'Earlidawn' | 8 | 3.7 | JK |
| Midland | 7 | 3.0 | K |
| NY 1570 | 1 | 2.0 | KL |
| 'Catskill' | 7 | 1.1 | L |

TABLE 3

Mean firmness measurement for NY 1529 and other cultivars

| Genotype | Mean puncture force (daltons) | |
|---|---|---|
| NY 1570 | 65.8 | A |
| 'NY 1529' | 62.7 | A |
| MDUS 4579 | 57.6 | A |
| MDUS 4774 | 56.4 | A |
| NY 1524 | 53.9 | AB |
| NY 1530 | 46.9 | BC |
| NY 1580 | 46.7 | BC |
| NY 1560 | 46.1 | BC |
| 'Holiday' | 45.7 | CD |
| 'Canoga' | 44.7 | CDE |
| MDUS 4426 | 44.2 | CDE |
| Allstar' | 39.3 | CDEF |
| NY 1431 | 38.3 | DEFG |
| 'Scott' | 37.6 | EFGH |
| NY 1406 | 35.9 | FGHI |
| 'Jewel' | 33.5 | FGHIJ |
| NY 1402 | 32.5 | FGHIJ |
| NY 1333 | 30.8 | GHIJ |
| NY 1482 | 30.1 | GHIJK |
| MDUS 4380 | 30.0 | HIJK |
| 'Honeoye' | 28.8 | IJK |
| MDUS 4355 | 28.7 | IJK |
| 'Lester' | 28.6 | IJK |
| 'Midland' | 27.1 | JKL |
| NY 1368 | 27.1 | JKL |
| 'Raritan' | 25.9 | JKL |
| 'Earlidawn | 25.6 | JKL |
| 'Sparkle' | 22.0 | KL |
| 'Catskill' | 19.9 | L |

TABLE 4

Mean berry weight for NY 1529 and other cultivars

| Genotype | Grams/berry | |
|---|---|---|
| NY 1524 | 14.4 | A |
| 'Canoga' | 13.7 | AB |
| 'Allstar' | 13.6 | AB |
| NY 1333 | 13.5 | ABC |
| MDUS 4426 | 13.4 | ABC |
| NY 1431 | 12.6 | ABCD |
| NY 1482 | 12.5 | ABCD |
| NY 1529 | 11.8 | BCDE |
| NY 1570 | 11.5 | CDEF |
| 'Jewel' | 11.3 | DEFG |
| 'Lester' | 11.2 | DEFG |
| NY 1580 | 11.2 | DEFG |
| NY 1406 | 10.9 | DEFGH |
| NY 1368 | 10.8 | DEFGHI |
| 'Holiday' | 10.7 | DEFGHIJ |
| NY 1560 | 10.5 | EFGHIJK |
| MDUS 4579 | 10.2 | EFGHIJKL |
| 'Honeoye' | 10.0 | EFGHIJKL |
| MDUS 4380 | 10.0 | EFGHIJKL |
| NY 1402 | 10.0 | EFGHIJKL |
| MDUS 4774 | 9.7 | FGHIJKL |
| 'Raritan' | 9.3 | GHIJKL |
| 'Scott' | 9.1 | HIJKL |
| MDUS 4355 | 9.0 | HIJKL |
| 'Catskill' | 8.9 | HIJKL |
| NY 1530 | 8.8 | IJKL |
| 'Midland' | 8.7 | JKL |
| 'Sparkle' | 8.6 | KL |
| 'Earlidawn' | 8.3 | L |

TABLE 5

Mean fruit appearance scores for NY 1529 and other cultivars

| Genotype | Replicates | Mean Score | |
|---|---|---|---|
| NY 1333 | 5 | 7.6 | A |
| 'Lester' | 7 | 7.3 | AB |
| 'Jewel' | 5 | 6.8 | ABC |
| NY 1524 | 6 | 6.5 | ABCD |
| NY 1530 | 6 | 6.3 | ABCD |
| MDUS 4355 | 6 | 6.3 | ABCDE |
| 'Honeoye' | 7 | 6.3 | ABCDE |

TABLE 5-continued

Mean fruit appearance scores for NY 1529 and other cultivars

| Genotype | Replicates | Mean Score |
|---|---|---|
| NY 1529 | 5 | 6.2 ABCDEF |
| MDUS 4380 | 6 | 6.2 BCDEF |
| 'Scott' | 8 | 6.1 BCDEF |
| NY 1368 | 5 | 6.0 BCDEF |
| NY 1560 | 4 | 5.8 CDEF |
| 'Raritan' | 7 | 5.7 CDEFG |
| 'Allstar' | 4 | 5.5 CDEFG |
| 'Canoga' | 4 | 5.5 CDEFG |
| 'Holiday' | 8 | 5.5 CDEFG |
| NY 1431 | 5 | 5.4 CDEFG |
| NY 1530 | 3 | 5.3 CDEFG |
| NY 1482 | 4 | 5.3 DEFG |
| NY 1402 | 5 | 5.0 EFG |
| NY 1406 | 9 | 4.9 FG |
| MDUS 4774 | 5 | 4.8 FG |
| 'Earlidawn' | 8 | 4.6 G |
| MDUS 4426 | 5 | 4.2 G |
| MDUS 4579 | 5 | 4.0 G |
| 'Midland' | 7 | 4.0 G |
| 'Sparkle' | 5 | 3.4 G |
| NY 1570 | 2 | 3.0 GH |
| 'Catskill' | 7 | 1.9 H |

TABLE 6

Mean flavor scores for NY 1529 and other cultivars

| Treatment | Replicates | Mean Score |
|---|---|---|
| 'Lester' | 7 | 6.3 A |
| NY 1570 | 2 | 6.0 AB |
| NY 1529 | 5 | 6.0 AB |
| 'Jewel' | 5 | 5.8 AB |
| 'Holiday' | 8 | 5.8 AB |
| NY 1368 | 5 | 5.6 AB |
| NY 1560 | 4 | 5.5 AB |
| 'Sparkle' | 5 | 5.4 AB |
| NY 1524 | 6 | 5.3 AB |
| 'Raritan' | 7 | 5.3 AB |
| 'Honeoye' | 7 | 5.1 AB |
| 'Allstar' | 4 | 5.0 AB |
| 'Canoga' | 4 | 5.0 AB |
| MDUS 4380 | 6 | 5.0 AB |
| 'Scott' | 8 | 4.9 AB |
| NY 1530 | 6 | 4.8 AB |
| MDUS 4355 | 6 | 4.8 AB |
| MDUS 4426 | 5 | 4.8 AB |
| NY 1333 | 5 | 4.8 AB |
| NY 1431 | 5 | 4.8 AB |
| NY 1580 | 3 | 4.7 AB |
| MDUS 4774 | 5 | 4.6 B |
| NY 1402 | 5 | 4.6 B |
| 'Midland' | 7 | 4.4 B |
| NY 1406 | 9 | 4.2 B |
| NY 1482 | 4 | 4.0 B |
| 'Catskill' | 7 | 4.0 B |
| MDUS 4579 | 5 | 3.8 B |
| 'Earlidawn' | 8 | 3.8 B |

TABLE 7

Mean fruit yield of 29 strawberry genotypes in 1981 (established under adverse growing conditions) and in 1982 (Established under favorable conditions)

| Genotype | Yield 1981 (g/4.5 m)[1] | Yield 1982 (g/4.5 m) |
|---|---|---|
| Allstar | 3197 abc | 6592 efghi |
| Canoga | 4321 ab | 10876 a |
| Catskill | 5268 a | 9830 abcd |
| Earlidawn | 3322 abc | 7133 cdefghi |
| Holiday | 3394 abc | 9750 abcd |
| Honeoye | 2760 abc | 10396 ab |
| Lester | 2762 abc | 6481 efghi |
| MDUS 4355 | 2594 abc | 5131 hij |
| MDUS 4380 | 2272 abc | 5038 ij |
| MDUS 4426 | 2883 abc | 5422 ghij |
| MDUS 4579 | 3150 abc | 8177 abcdefg |
| MDUS 4774 | 2069 bc | 4599 ij |
| Midland | 3479 abc | 5149 hij |

TABLE 7-continued

Mean fruit yield of 29 strawberry genotypes in 1981 (established under adverse growing conditions) and in 1982 (Established under favorable conditions)

| Genotype | Yield 1981 (g/4.5 m)[1] | Yield 1982 (g/4.5 m) |
|---|---|---|
| Jewel | 5166 ab | 6407 efghi |
| NY 1333 | 2113 abc | 6064 fghi |
| NY 1368 | 3148 abc | 6841 efghi |
| NY 1402 | 2450 abc | 7089 defghi |
| NY 1406 | 4616 ab | 10748 a |
| NY 1431 | 2744 abc | 8359 abcdef |
| NY 1482 | 5171 ab | 7874 bcdefgh |
| NY 1524 | 2622 abc | 7234 cdefghi |
| NY 1529 | 3542 abc | 10824 a |
| NY 1530 | 5010 ab | 9674 abcd |
| NY 1560 | 2458 abc | 6418 efghi |
| NY 1570 | 1125 c | 2749 j |
| NY 1580 | 2309 abc | 9834 abcd |
| Raritan | 3383 abc | 9933 abc |
| Scott | 4270 abc | 8347 abcdef |
| Sparkle | 3942 abc | 8943 abcde |

[1]To convert to lb/A multiply by 1.6

TABLE 8

Summary of results from 1981 and 1982 taste panel evaluations of frozen fruit.

1. Consistently rated 'very good'
   MDUS 4744
   Holiday
   Honeoye
   MDUS 4355
   NY 1406
2. Consistently rate 'good'
   Scott
   NY 1529
   Jewel
3. Marginally 'acceptable'
   NY 1580
   Sparkle
   Lester
   NY 1570
   NY 1482
   NY 1524
   NY 1402
   Midland
4. 'Unacceptable'
   Canoga
   Allstar
   Raritan
   NY 1333
   NY 1560
   MDUS 4579
   NY 1530
   NY 1368
   MDUS 4426
   NY 1431
   MDUS 4380
   Earlidawn
   Catskill

TABLE 9

Overall genotype mean rankings (yield, size, attractiveness, skin, flesh, fresh flavor, frozen quality) listed in order of total mean ranking of overall traits.

| Overall ranking | cultivar/ selection | Yield[1] rank | Yield[2] rank | Size[3] rank | Attractiveness[4] rank |
|---|---|---|---|---|---|
| 1 | NY 1529 | 9 | 2 | 2 | 8 |
| 2 | Holiday | 11 | 8 | 13 | 16 |
| 3 | Jewel | 3 | 22 | 18 | 3 |
| 4 | NY 1524 | 21 | 15 | 8 | 4 |
| 5 | Canoga | 6 | 1 | 1 | 15 |
| 6 | NY 1530 | 4 | 9 | 19 | 5 |
| 7 | Scott | 7 | 12 | 16 | 10 |
| 8 | NY 1406 | 5 | 3 | 17 | 21 |
| 9 | MDUS 4359 | 18 | 20 | 11 | 2 |
| 10 | Honeoye | 19 | 4 | 20 | 7 |

TABLE 9-continued

Overall genotype mean rankings (yield, size, attractiveness, skin, flesh, fresh flavor, frozen quality) listed in order of total mean ranking of overall traits.

| | | | | | |
|---|---|---|---|---|---|
| 11 | NY 1580 | 25 | 6 | 10 | 18 |
| 12 | Allstar | 14 | 19 | 7 | 14 |
| 13 | NY 1482 | 2 | 14 | 6 | 19 |
| 14 | NY 1368 | 16 | 18 | 15 | 11 |
| 15 | MDUS 4579 | 15 | 13 | 12 | 25 |
| 16 | MDUS 4426 | 17 | 24 | 5 | 24 |
| 17 | NY 1333 | 27 | 23 | 3 | 1 |
| 18 | MDUS 4355 | 22 | 26 | 24 | 6 |
| 19 | MDUS 4774 | 28 | 28 | 14 | 22 |
| 20 | Raritan | 12 | 5 | 22 | 13 |
| 21 | NY 1560 | 23 | 21 | 21 | 12 |
| 22 | NY 1570 | 29 | 29 | 4 | 28 |
| 23 | NY 1431 | 20 | 11 | 9 | 17 |
| 24 | Sparkle | 8 | 10 | 28 | 27 |
| 25 | NY 1402 | 24 | 17 | 25 | 20 |
| 26 | MDUS 4380 | 26 | 27 | 23 | 9 |
| 27 | Catskill | 1 | 7 | 27 | 29 |
| 28 | Midland | 10 | 25 | 26 | 25 |
| 29 | Earlidawn | 13 | 16 | 29 | 23 |

| Overall ranking | cultivar/ selection | Skin[5] rank | Texture[6] rank | Flavor[7] rank | Quality[8] rank |
|---|---|---|---|---|---|
| 1 | NY 1529 | 2 | 2 | 3 | 9 |
| 2 | Holiday | 8 | 9 | 5 | 1 |
| 3 | Jewel | 3 | 16 | 4 | 9 |
| 4 | NY 1524 | 1 | 5 | 9 | 19 |
| 5 | Canoga | 10 | 10 | 13 | 29 |
| 6 | NY 1530 | 4 | 6 | 16 | 29 |
| 7 | Scott | 11 | 14 | 15 | 9 |
| 8 | NY 1406 | 15 | 15 | 25 | 1 |
| 9 | MDUS 4359 | 12 | 23 | 1 | 19 |
| 10 | Honeoye | 23 | 21 | 11 | 1 |
| 11 | NY 1580 | 9 | 7 | 21 | 19 |
| 12 | Allstar | 13 | 12 | 12 | 29 |
| 13 | NY 1482 | 18 | 19 | 26 | 19 |
| 14 | NY 1368 | 6 | 25 | 6 | 29 |
| 15 | MDUS 4579 | 7 | 3 | 28 | 29 |
| 16 | MDUS 4426 | 5 | 11 | 18 | 29 |
| 17 | NY 1333 | 14 | 18 | 19 | 29 |
| 18 | MDUS 4355 | 16 | 22 | 17 | 1 |
| 19 | MDUS 4774 | 17 | 4 | 22 | 1 |
| 20 | Raritan | 22 | 26 | 10 | 29 |
| 21 | NY 1560 | 19 | 8 | 7 | 29 |
| 22 | NY 1570 | 28 | 1 | 2 | 19 |
| 23 | NY 1431 | 21 | 13 | 20 | 29 |
| 24 | Sparkle | 25 | 28 | 8 | 19 |
| 25 | NY 1402 | 20 | 17 | 23 | 19 |
| 26 | MDUS 4380 | 24 | 20 | 14 | 29 |
| 27 | Catskill | 29 | 29 | 27 | 29 |
| 28 | Midland | 27 | 24 | 24 | 19 |
| 29 | Earlidawn | 26 | 27 | 29 | 29 |

[1]Yield based on 3 replicates, 15-ft. plots. 8 harvest dates, 1981.
[2]Yield based on 3 replicates, 15-ft. plots, 8 harvest dates, 1982.
[3]Size = total yield divided by total number of fruit.
[4]Attractiveness evaluated subjectively, scored 1–9, 4–8 reps.
[5]Skin toughness evaluated subjectively, scored 1–9, 4–8 reps.
[6]Texture evaluated using Instron Instrument, 12 fruit per mean, 4–8 reps.
[7]Flavor evaluated subjectively, score 1–9, 4–8 reps.
[8]Frozen quality evaluated by replicated blind taste panels, 1 = very good, 9 = good, 19 = acceptable, 29 = unacceptable.

TABLE 10

NY 1529 as scored at various sites in the Great lakes region of North America.

| Test site | Yield | Flavor | Size | Appearance | Firm-ness |
|---|---|---|---|---|---|
| Montreal, Quebec | 3 | 3 | 3 | 3 | 5 |
| MN | 4 | 2 | 3 | 3 | 5 |
| WS | 3 | 4 | 3 | 4 | — |
| MA | 5 | 3 | 4 | 4 | 4 |
| NY | 4 | 4 | 5 | 5 | 4 |
| OH | 5 | 4 | 4 | 4 | 4 |
| PA | 5 | 3 | 4 | 4 | 3 |
| Average Score: | 4.1 | 3.3 | 3.7 | 4.4 | 4.2 |

1 = poor, 3 = average, 5 = best

DESCRIPTION OF THE INVENTION

This invention is a new and distinct variety of strawberry (Fragaria×Ananassa) which is exceptional in combining large yield, potential large fruit size, extreme fruit firmness, and good fruit quality. The strawberry is named 'Seneca' and was tested as NY 1529. Asexual propagation has been achieved by runner plants and also by means of tissue culture at the Department of Horticultural Sciences, Cornell University, Geneva, N.Y.

The primary berries of NY 1529 are blunt conic in shape with very broad-shoulders, the smaller fruit are near globose in shape. Seeds are mostly dull-yellow and may be dark red on the dark side of the fruit, are slighly sunken to even with the skin, and are more often even toward the fruit tip. The calyx is even to sunken, not reflexed. Sepals rest on top of fruit and tend to lay flatter as fruit mature. Sepal tips may turn upward until fruit mature. Skin has moderate toughness, flesh is very firm, exterior color is medium red and glossy, corresponding to Red 45A and 46B of the Royal Horticultural Society (London) Colour Chart. Internal flesh is a very light red transparent color. Fruit flavor is good, slightly acid with a mild 'Holiday' aromatic quality. NY 1529 matures in late midseason.

NY 1529 has a moderate vigor and runnering growth habit, its leaves are medium green in color, corresponding to Green 137B of the R.H.S. Colour Chart and foliage is open not cupped. NY 1529 leaf serrations are less deeply serrated in comparison with 'Earliglow'. Glandular hairs on the flower pedicil epidermis of NY 1529 run almost parallel with the pedicel. The glandular hairs of NY 1529 are less dense than 'Allstar'.

Figure 1:
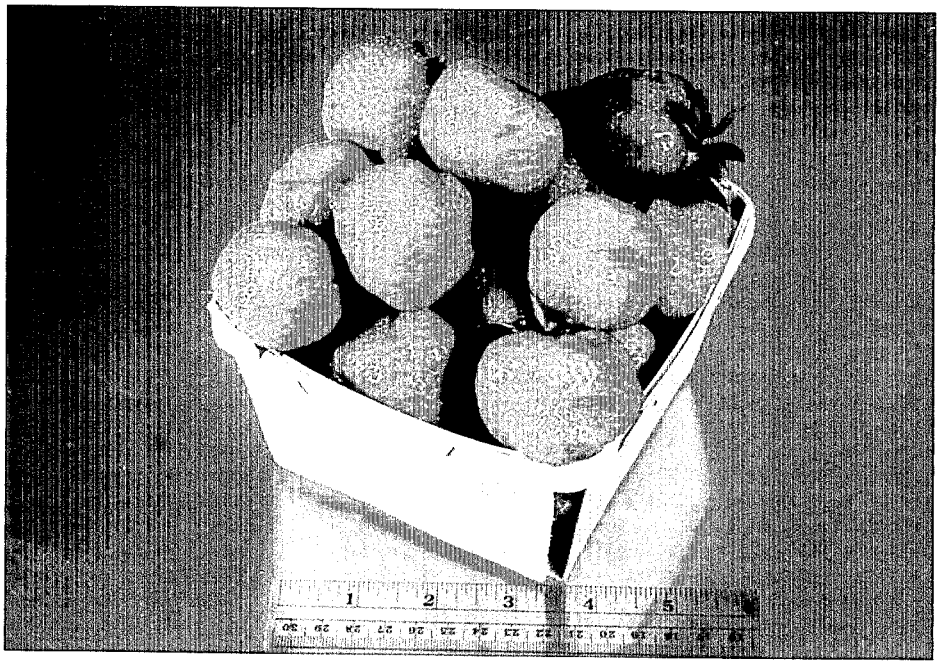
FIG. 1. One quart basket of NY 1529 shown with scale in inches and millimeters. Note large size, glossy color, and attractive appearance and shape.
Figure 2:
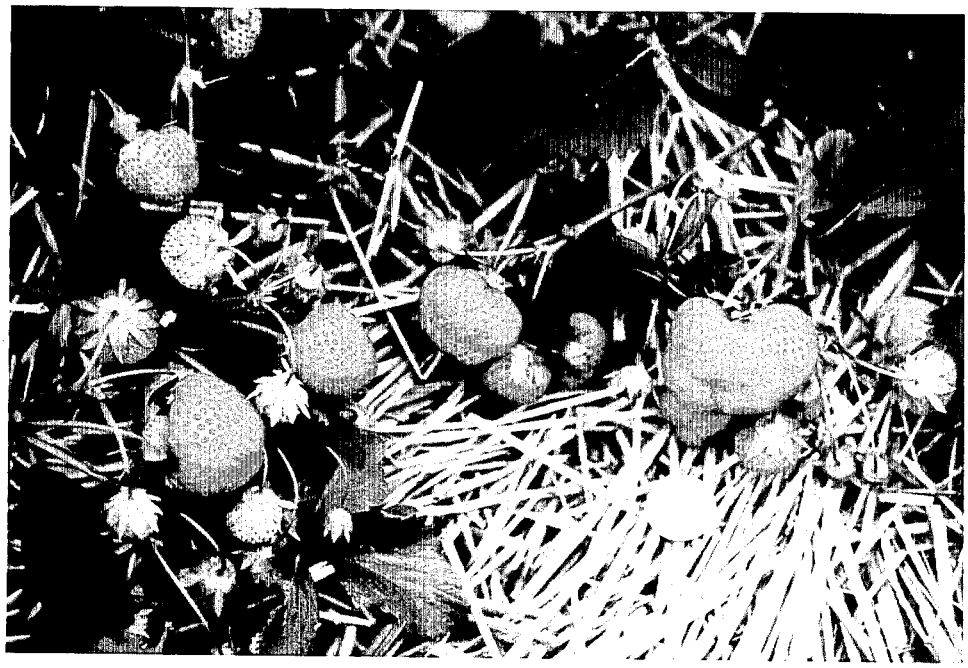
FIG. 2. Fruit shown ripening in a field planting. Note fruit size in comparison to the quarter, and fruit ripen over a long period.
Figure 3:
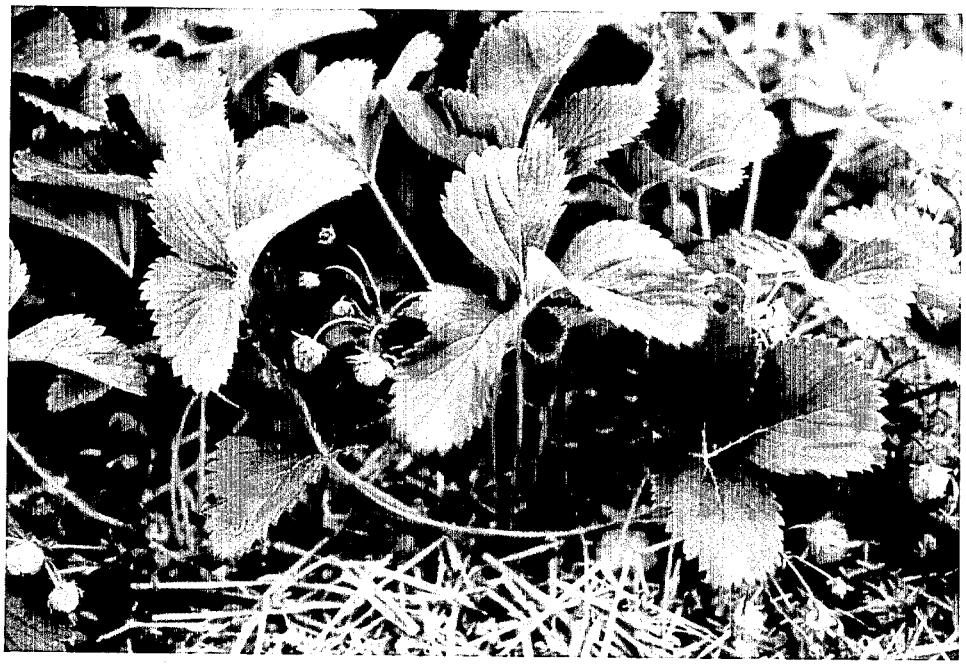
FIG. 3. Foliage shown in a field planting. Note open canopy, leaves not cupped.
Figure 5:
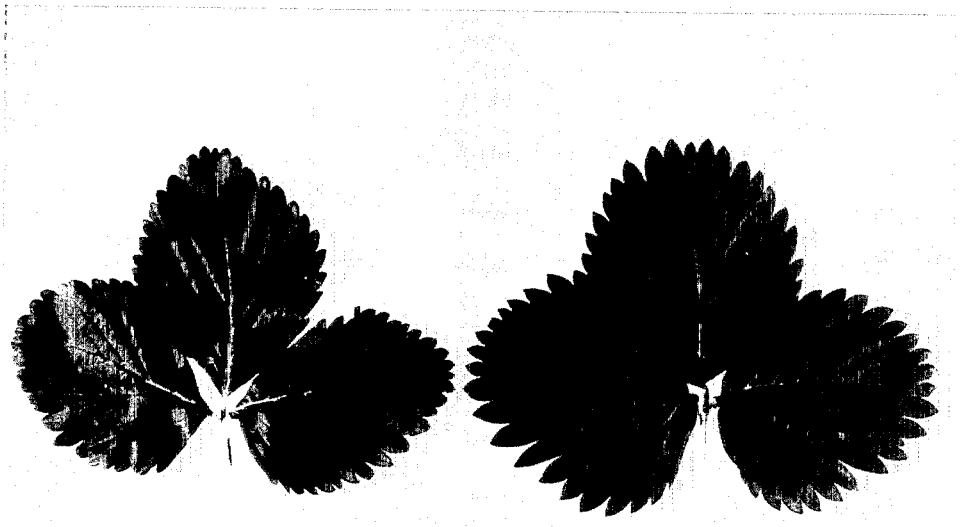
FIG. 5. NY 1529 leaf serrations in comparison with 'Earliglow'. 'Earliglow' (on the right) is more deeply serrated along the leaf edge.
Figure 4:
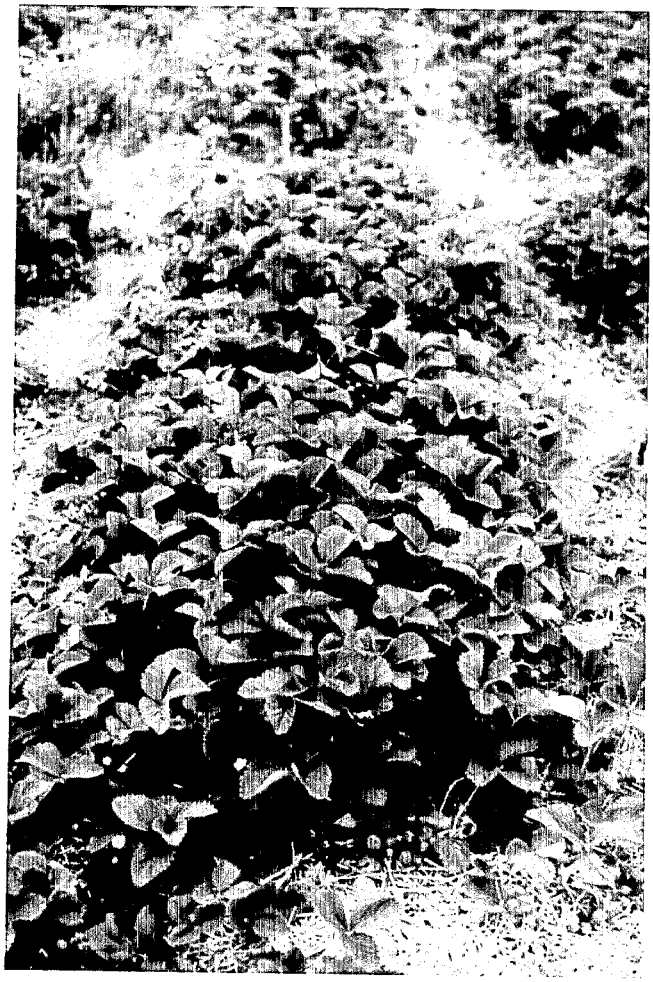
FIG. 4. Plot of NY 1529 with moderate vigor and runnering, very acceptable habit for production in the Northeast.
Figure 6:
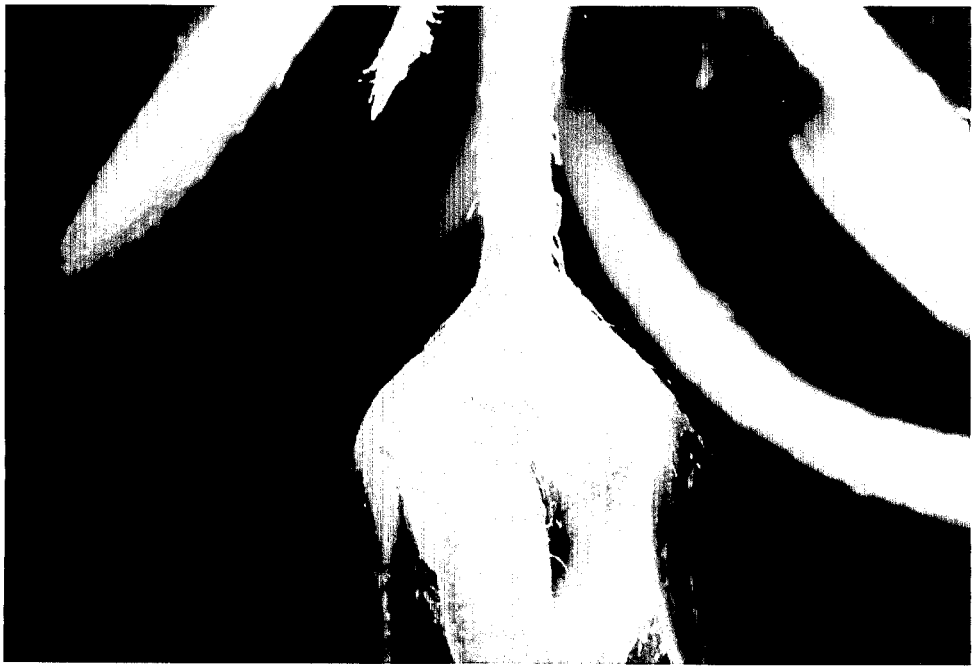
FIG. 6. Glandular hairs on the flower pedicel and peduncle of NY 1529 run almost parallel with the pedicel, similar to 'Earliglow'.
Figure 7:
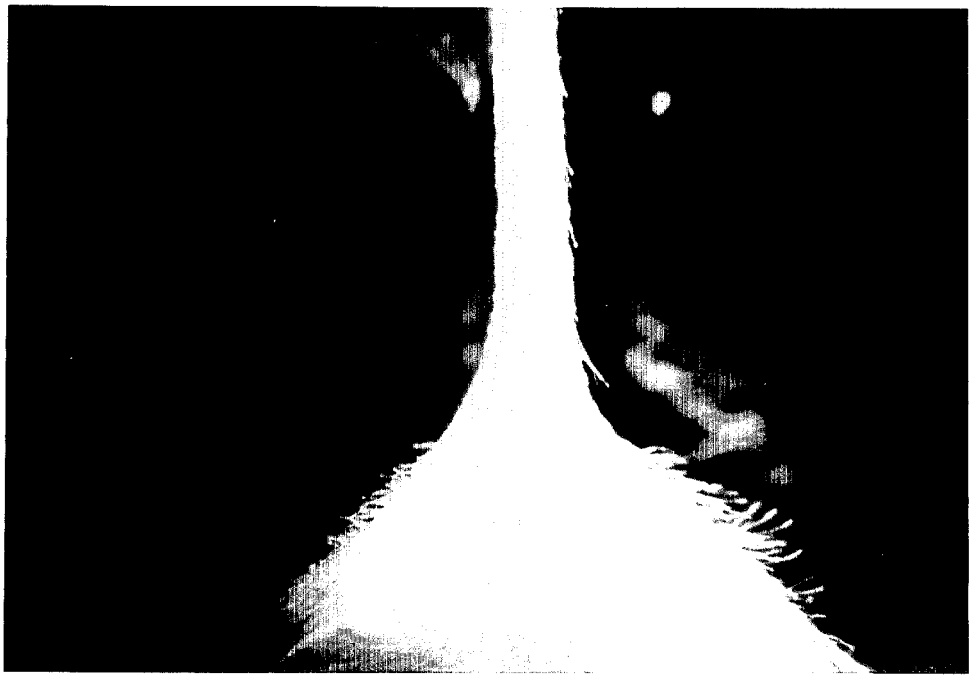
FIG. 7 (PRIOR ART)
FIG. 7. Note the way the glandular hairs on 'Earliglow' run parallel to the pedicel.
Figure 8:
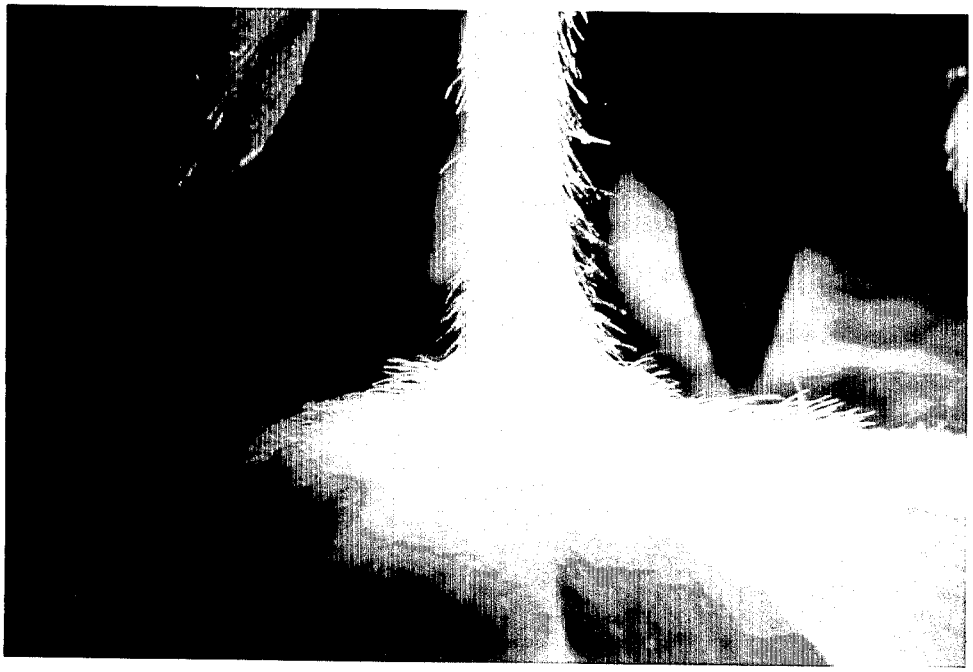
FIG. 8 (PRIOR ART)
FIG. 8. The amount of grandular hairs on NY 1529 (photo 6), is much less dense than 'Allstar', shown here.
Figure 9:
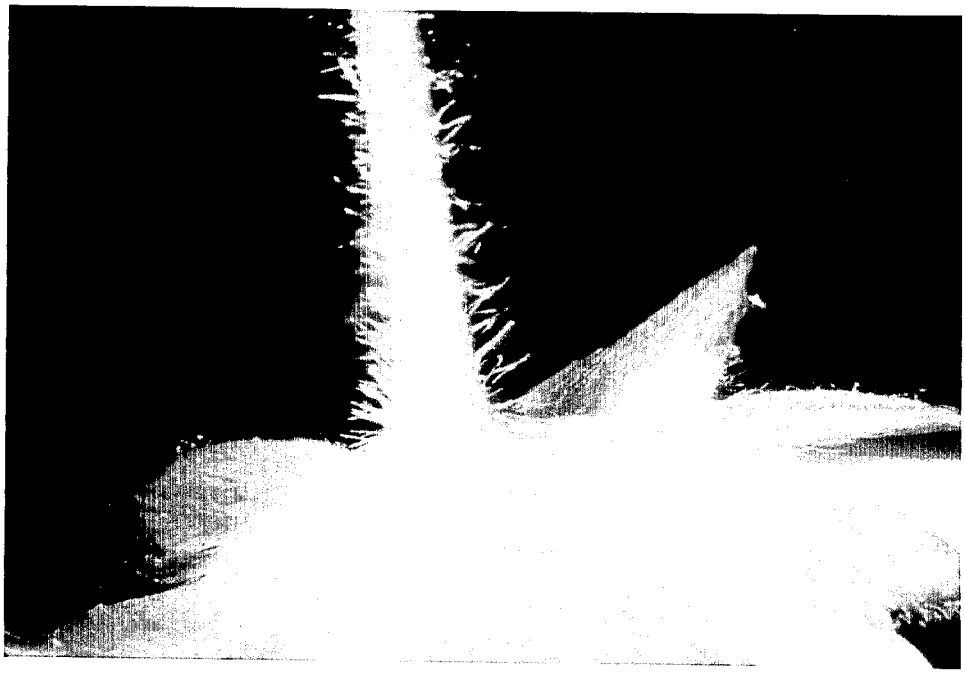
FIG. 9 (PRIOR ART)
FIG. 9. In contrast to FIGS. 6 and 7, glandular hairs on 'Honeyoye' are perpendicular to the pedicel and may be pointed slightly downward or more than 90 degrees. This is similar to NY 1593, except NY 1593 glandular hairs are pointed slightly upward and less than 90 degrees from the pedicel.
Figure 10:
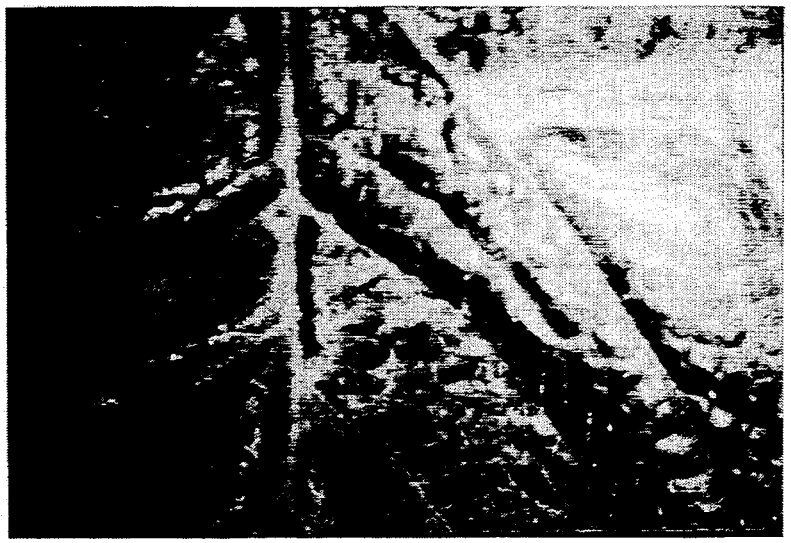
FIG. 10. Microphotograph of the upper leaf surface of 'Seneca'.
Figure 11:
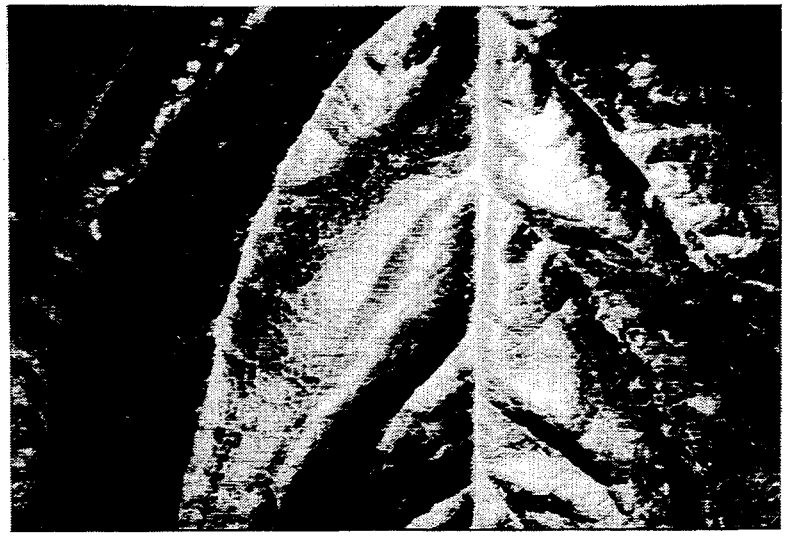
FIGURE 11 (PRIOR ART)
FIG. 11. Microphotograph of the upper leaf surface of 'Allstar'.

Further examination of 'Seneca' leaves revealed a few more distinguishing characteristics. FIG. 10 shows the upper surface of a 'Seneca' strawberry leaf with moderate pubescence, compared to FIG. 11 showing the upper surface of an 'Allstar' strawberry leaf with no pubescence present. Upon microscopic examination of the upper leaf surfaces, 'Seneca' always shows a moderate amount of pubescence and 'Allstar' is absent of any pubescence on the upper leaf surface.

Figure 12:
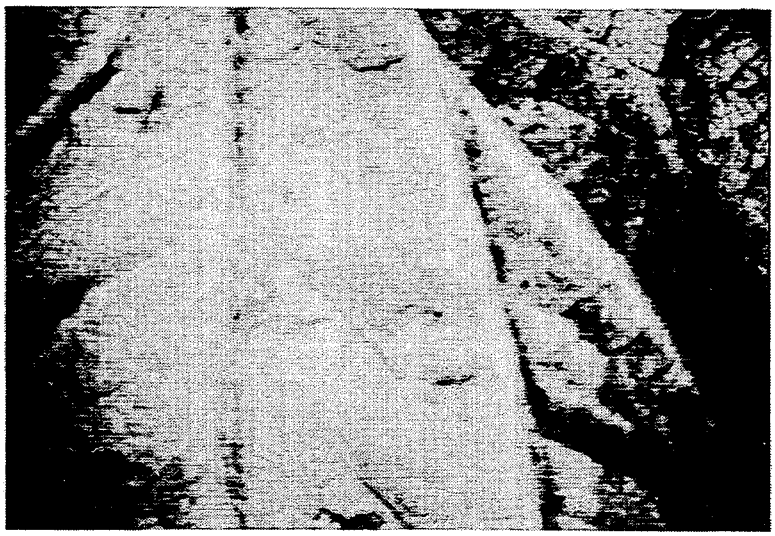
FIG. 12. Microphotograph of the lower leaf surface of 'Seneca'.
Figure 13:
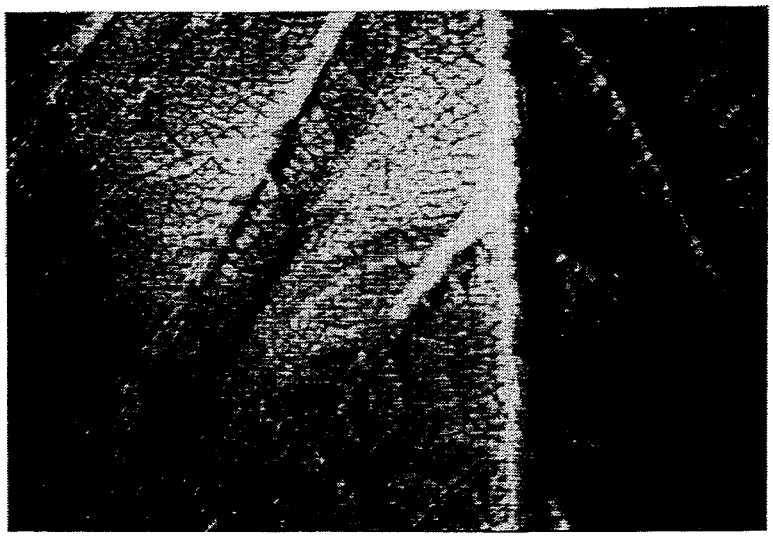
FIGURE 13 (PRIOR ART)
FIG. 13. Microphotograph of the lower leaf surface of 'Allstar'.
Figure 14:
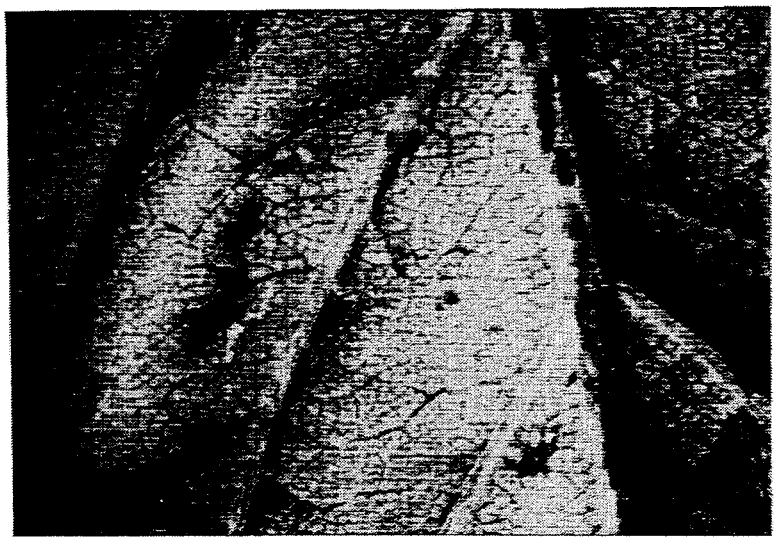
FIGURE 14 (PRIOR ART)
FIG. 14. Microphotograph of the lower leaf surface of 'Honeyoye'.
Figure 15:
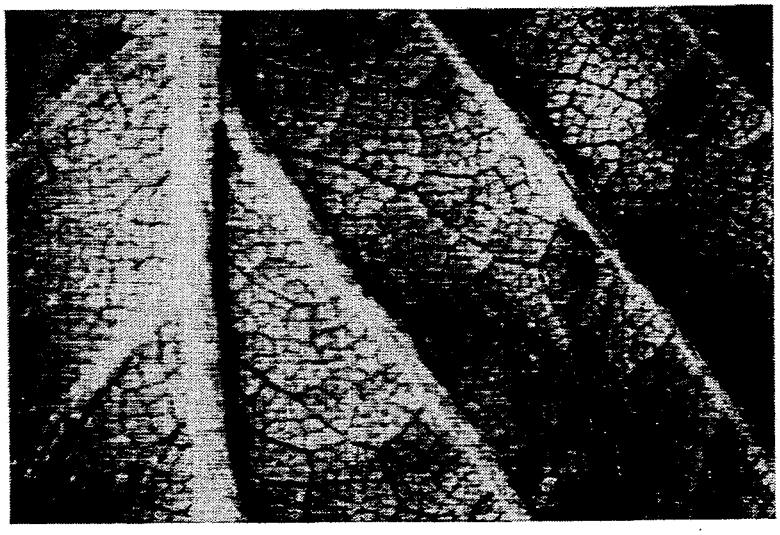
FIGURE 15 (PRIOR ART)
FIG. 15. Microphotograph of the lower leaf surface of 'Earliglow'.
Figure 16:
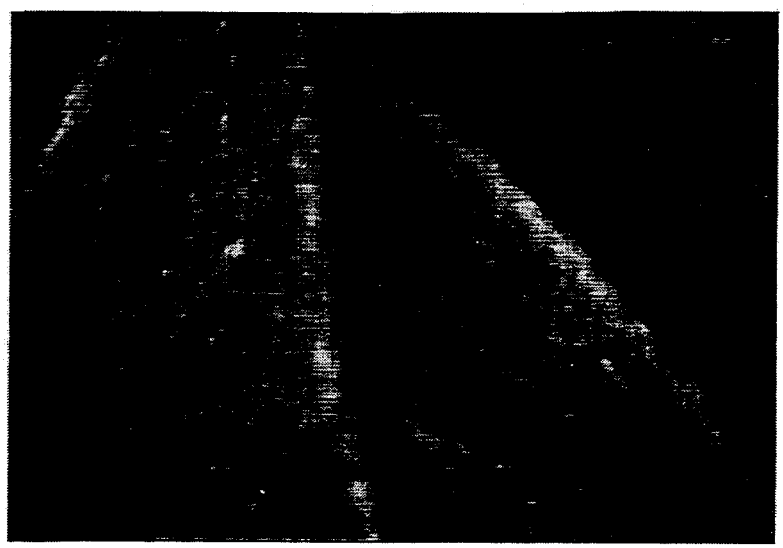
FIGURE 16 (PRIOR ART)
FIG. 16. Microphotograph of the lower leaf surface of 'Jewel'.

FIG. 12 shows the lower leaf surface of 'Seneca' with no interveinal pubescence and few veinal hairs running parallel and on the lower leaf venation, compared to 'Allstar' in FIG. 13 which has many interveinal hairs and more dense and coarse venal pubescence. FIG. 14 shows the undersurface of a 'Honeoye' leaf and has similar veinal and interveinal pubescence as 'Allstar'. 'Earliglow' (FIG. 15), and 'Jewel' (FIG. 16), (as well as 'Chambly', 'Cavendish', and 'Lateglow') all have less interveinal pubescence than 'Allstar' and 'Honeoye', but more than 'Seneca'.

Mature 'Seneca' upper leaf surfaces correspond to green 137 B of the R.H.S. Colour Chart and lower surfaces correspond to Greyed-Green 191 A. Younger and newly unfurled leaves correspond to Green 137 D for the upper leaf surface and Greyed-Green 191 B for the lower leaf surface.

'Seneca' leaflet size ranges in length from 8.1–9.5 cm (average length 8.54 cm) and ranges in width from 5.9–9.5 cm (average width 7.06 cm) with an average of 28.88 serrations per leaflet. Average serration width is 0.93 cm.

'Seneca' has no brown resistance to any root diseases including Red Steele and verticillium wilt and seems particularly susceptible to Black Root Rot disease. Therefore, it should not be planted into solid known to be infested up such root disease organisms.

Usefulness

This new cultivar is particularly well-suited for use by commercial fruit growers in the Great Lakes Region of the United States, because of its high potential (Table 7), its tough skin (Table 2) and firm flesh (Table 3) which are needed for shipping, its large fruit size (Table 4) which is needed for efficient hand harvest, and its attractive (Table 5) and pleasant flavored (Table 6) fruit which should market well. Cooperative testers in many Great Lakes States report superior performance (Table 10), indicating good hardiness. In addition, taste panels have found this cultivar to be superior to most other cultivars tested in terms of frozen fruit quality (Table 8). When 29 cultivars and selections adapted to the Great Lakes climate were ranked for 8 characteristics, this cultivar was found to make the highest mean ranking for all characters (Table 9).

We claim:

1. The new and distinct variety of strawberry herein described and illustrated and identified by the characters enumerated above.

* * * * *